(12) United States Patent
Sun et al.

(10) Patent No.: US 9,696,361 B1
(45) Date of Patent: Jul. 4, 2017

(54) METHOD AND APPARATUS FOR ANALYZING FEATURES OR CHARACTERISTICS OF A CABLE IN A NETWORK

(71) Applicant: MARVELL INTERNATIONAL LTD., Hamilton (BM)

(72) Inventors: Junqing Sun, Fremont, CA (US); Danjin Wu, Sunnyvale, CA (US); Hung Nguyen, San Jose, CA (US)

(73) Assignee: MARVELL INTERNATIONAL LTD. (BM)

( * ) Notice: Subject to any disclaimer, the term of this patent is extended or adjusted under 35 U.S.C. 154(b) by 155 days.

(21) Appl. No.: 14/566,756

(22) Filed: Dec. 11, 2014

Related U.S. Application Data

(60) Provisional application No. 61/914,633, filed on Dec. 11, 2013.

(51) Int. Cl.
*G01R 31/02* (2006.01)
*G01R 27/28* (2006.01)
*G01N 22/00* (2006.01)

(52) U.S. Cl.
CPC ......... *G01R 31/021* (2013.01); *G01N 22/00* (2013.01); *G01R 27/28* (2013.01)

(58) Field of Classification Search
CPC ......... G01R 31/02; G01R 27/28; G01N 22/00
See application file for complete search history.

(56) References Cited

U.S. PATENT DOCUMENTS

| 5,245,291 A * | 9/1993 | Fujimura | G01B 7/026 324/617 |
| 6,614,236 B1 * | 9/2003 | Karam | G01R 31/08 324/532 |
| 7,808,247 B1 * | 10/2010 | Lo | G01R 31/021 324/533 |
| 8,582,443 B1 * | 11/2013 | Sun | H04L 43/16 370/242 |
| 2006/0181283 A1 * | 8/2006 | Wajcer | H04B 3/46 324/539 |
| 2010/0070228 A1 * | 3/2010 | Chappell | H04N 7/173 702/79 |

* cited by examiner

*Primary Examiner* — Jeff Natalini

(57) ABSTRACT

Systems, methods, and other embodiments associated with testing a cable are described. According to one embodiment, an integrated circuit device includes a transmitter, a receiver, cable tester logic and a cable test control logic. The transmitter is configured to transmit signals to a cable. The receiver is configured to receive signals from the cable. The cable tester logic includes an echo tester configured to identify peaks corresponding to echo canceller coefficients that model an impulse response of reflected signals received by the receiver and a power-based cable tester configured to determine a power-based cable length based on an attenuation of a signal received from the link partner. The cable test control logic is configured to selectively activate one or both of the echo tester and the power-based tester and to determine a cable length based, at least in part, on the power-based cable length and the identified peaks.

19 Claims, 8 Drawing Sheets

US 9,696,361 B1

METHOD AND APPARATUS FOR ANALYZING FEATURES OR CHARACTERISTICS OF A CABLE IN A NETWORK

CROSS REFERENCE TO RELATED APPLICATIONS

This patent disclosure claims the benefit of U.S. Provisional Application Ser. No. 61/914,633 filed on Dec. 11, 2013, which is hereby wholly incorporated by reference.

BACKGROUND

A cable tester is commonly used to determine particular features or characteristics of a cable—e.g., a length of cable, whether or not a fault exists in the cable, and so on. A conventional hand-operated (portable) cable tester is typically manually coupled by a first connector (such as an RJ-45 or other connector) to a "head side" of a cable, and a second connector at the other end of the cable (called the "tail side") connects the cable to a load. Such a cable tester typically requires the load to be a remote node terminator or a loop back module, and the cable tester can be used perform an analysis of the cable, detecting a short, an open, a crossed pair, or a reversed pair.

A short condition occurs when two or more lines are short-circuited together. An open condition occurs when there is a lack of continuity between both ends of a cable. A crossed pair occurs when a cable pair communicates with different pins at each end of a cable.

SUMMARY

In general, in one aspect this specification discloses an apparatus. The apparatus includes a transmitter, a receiver, a cable tester, and a cable test control logic. The transmitter is configured to transmit signals to a link partner by way of a cable. The receiver is configured to receive signals from the link partner by way of the cable. The cable tester is connected to the transmitter and the receiver. The cable tester includes an echo cable tester configured to, in response to a first signal being transmitted along the cable by the transmitter, identify peaks in a second signal received by the receiver, wherein the second signal corresponds to a reflection of the first signal within the cable, and wherein the peaks are identified based on echo canceller coefficients. The cable tester also includes a power-based cable tester configured to determine a length of the cable based on an attenuation of a signal received from the link partner. The cable test control logic is configured to define an end detection range based, at least in part, on the length of the cable as determined by the power-based cable tester, determine that a peak falls within the end detection range, designate the peak as corresponding to a terminator of the cable, and determine a length of the cable based, at least in part, on the designated peak.

In general, in another aspect, this specification discloses a method for determining the length of a cable. The method includes determining a power-based cable length of a cable based on signal attenuation of a signal received on the cable from a link partner and defining an end detection range based, at least in part, on the power-based cable length. Peaks in a reflected signal on the cable are identified using echo canceller coefficients and a peak that falls within the end detection range is determined. The method includes designating the peak as corresponding to a cable terminator and determining a length of the cable based, at least in part, on the designated peak.

In general, in another aspect, this specification discloses an integrated circuit device for testing a cable. The integrated circuit device includes a transmitter, a receiver, cable tester logic and a cable test control logic. The transmitter is configured to transmit signals to a cable. The receiver is configured to receive signals from the cable. The cable tester logic includes an echo tester configured to identify peaks corresponding to echo canceller coefficients that model an impulse response of reflected signals received by the receiver and a power-based cable tester configured to determine a power-based cable length based on signal attenuation of a signal received from the link partner. The cable test control logic is configured to selectively activate one or both of the echo tester and the power-based tester and to determine a cable length based, at least in part, on the power-based cable length and the identified peaks.

BRIEF DESCRIPTION OF THE DRAWINGS

The accompanying drawings, which are incorporated in and constitute a part of the specification, illustrate various systems, methods, and other embodiments of the disclosure. Illustrated element boundaries (e.g., boxes, groups of boxes, or other shapes) in the figures represent one example of the boundaries. In some examples one element may be designed as multiple elements or multiple elements may be designed as one element. In some examples, an element shown as an internal component of another element may be implemented as an external component and vice versa.

DETAILED DESCRIPTION

Figure 1:
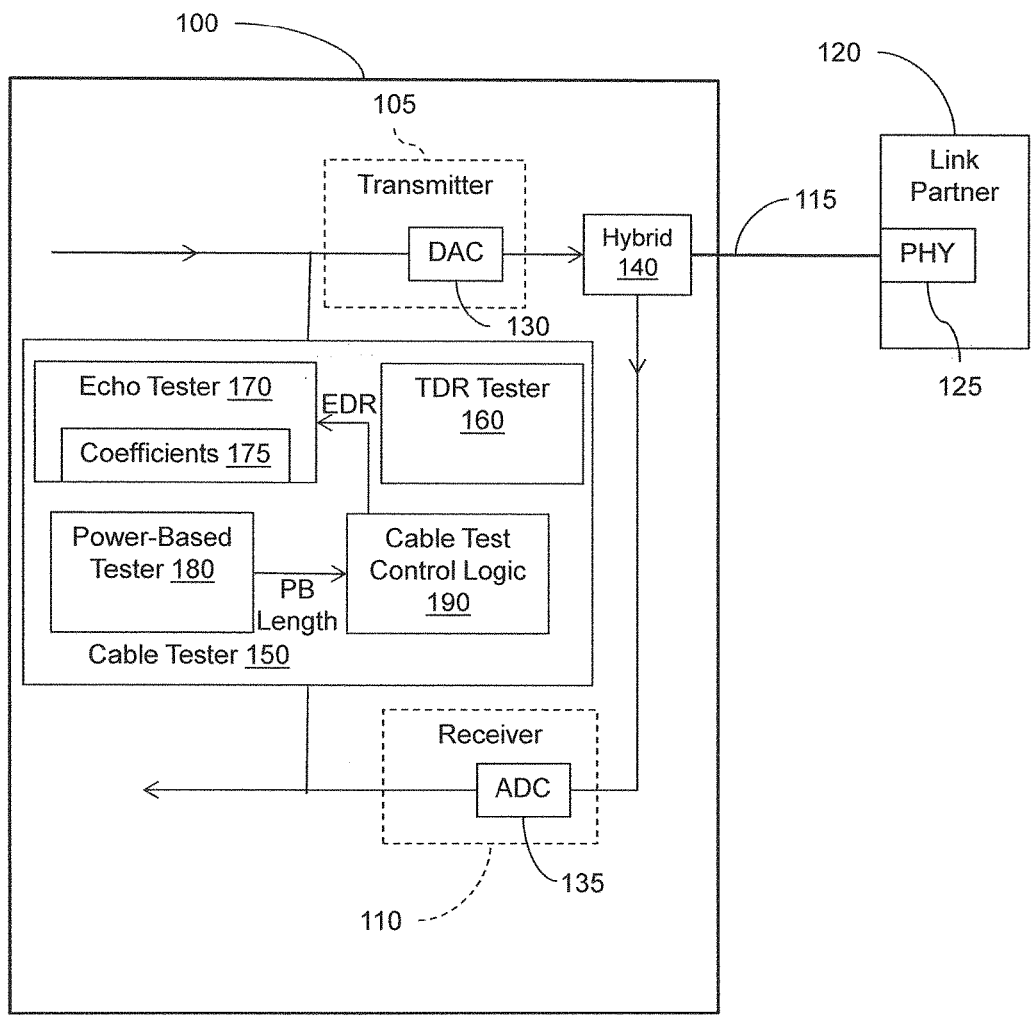
FIG. 1 illustrates one embodiment of an apparatus associated with a power-based virtual cable test.

Ethernet network devices such as switches, routers, and network appliances include physical layer devices with ports that connect to a cable. Virtual Cable Test (VCT) technology exists that is built into the physical layer of these devices and allows an Ethernet PHY to check the quality of a cable connection without the need to unplug the cable, insert a cable tester, and loop back the cable far ends. Many such VCT testers are based on Time Domain Reflectometry technology (TDR), in which the VCT tester sends a test pulse into the cable and analyzes a reflected signal to identify features of the cable. However, TDR is insensitive to minor faults in a cable. For example, a TDR test sometimes does not find a cable connection failure even though the cable impedance mismatch affects Ethernet performance. Also, when performing a TDR cable test, the test pulse may disturb the actual network data on the cable. Thus the network is typically shut down during a cable test, which may be inconvenient.

Echo canceller coefficient-based VCT finds peaks in a reflected signal based on echo canceller coefficients determined by echo cancelling signal processors in the device. The amplitude and location of the peaks are used to locate faults and determine a length of the cable. The highest peak is typically identified as the end connector or terminator of the cable and smaller peaks are identified as faults. Because it utilizes echo cancelling signal processors that operate to cancel echoes in network traffic, echo canceller coefficient-based VCT can be used while the cable is carrying normal network traffic. However, when a cable is long (meaning that the corresponding peak may be small) it may be difficult to distinguish peaks from noise caused by normal network traffic in the channel. Further, in some circumstances, a fault in the cable that is close to the head side may create a large peak that dwarfs a smaller peak created by a remote cable terminator, resulting in the large peak being used to calculate a length of the cable, in which case the length of the cable would be erroneously determined to be shorter than an actual length of the cable.

Described herein are example systems, methods, and other embodiments associated with testing for features of a cable—e.g., a length of a cable, whether a fault exists in a cable length, and so on. In one embodiment, a physical layer device is configured to detect a length of a cable and identify a fault in the cable by selectively combining power-based cable length estimation and echo canceller coefficient-based cable fault and end detection. In one embodiment, the device determines a power-based estimate of the length of the cable and uses the estimated length to define an end detection range. The end detection range defines a region of the cable in which a terminator of the cable is expected to fall (e.g., the terminator is expected at the end of the cable as roughly determined using the power-based estimate). The locations of peaks identified in a reflected signal by analyzing echo canceller coefficients are compared to the end detection range. A peak that falls within the end detection range is classified as corresponding to the cable's terminator. Peaks that fall outside the end detection range are classified as faults. In one embodiment, TDR cable fault testing, power-based cable length estimation, and echo canceller coefficient-based fault and end detection are selectively combined to provide optimal cable test results in many different testing scenarios.

With reference to FIG. 1, one embodiment of an apparatus 100 is shown that is configured to detect faults in a cable. The apparatus 100 may be a physical layer device (e.g. Ethernet PHY), a digital signal processor (DSP), a transceiver, a network communication device, and so on. The apparatus 100 includes a transmitter 105 and a receiver 110 that are configured for connection to a cable 115 (e.g., twisted pair cable) via a port. Communication lines through the transmitter 105 and the receiver 110 define a transmission path and a receiving path, respectively. The cable 115 can be used to connect the apparatus 100 to a remote device (link partner 120) that includes a PHY 125. The transmitter 105 includes a digital-to-analog converter (DAC) 130 for converting outgoing transmission signals to analog form. The receiver 110 includes an analog-to-digital converter (ADC) 135 for converting incoming analog signals to digital form.

In one embodiment, the apparatus 100 is implemented on a chip including one or more integrated circuits or other logic components configured to perform one or more of the functions described herein. The apparatus 100 may be implemented in an electronic device (e.g. computer, laptop, printer, hand held device, and so on) that can be connected to a cable and is able to communicate with a link partner.

In one embodiment, the transmitter 105 and receiver 110 are connected to a hybrid circuit 140. The hybrid circuit 140 controls access to the communication channel (e.g. cable 115 with four twisted pair wires) for full-duplex bi-directional operation over the twisted pair cable.

The apparatus 100 includes a cable tester 150 configured to determine the length of, and/or identify any faults in, the cable 115. The cable tester 150 includes a TDR tester 160, an echo tester 170, a power based tester 180, and a cable test control logic 190. As will be described in more detail below, the cable test control logic 190 selectively activates one or more of the TDR tester 160, the echo tester 170, and the power based tester 180 and reports cable length and/or faults based on results provided by the activated tester(s).

Figure 2:
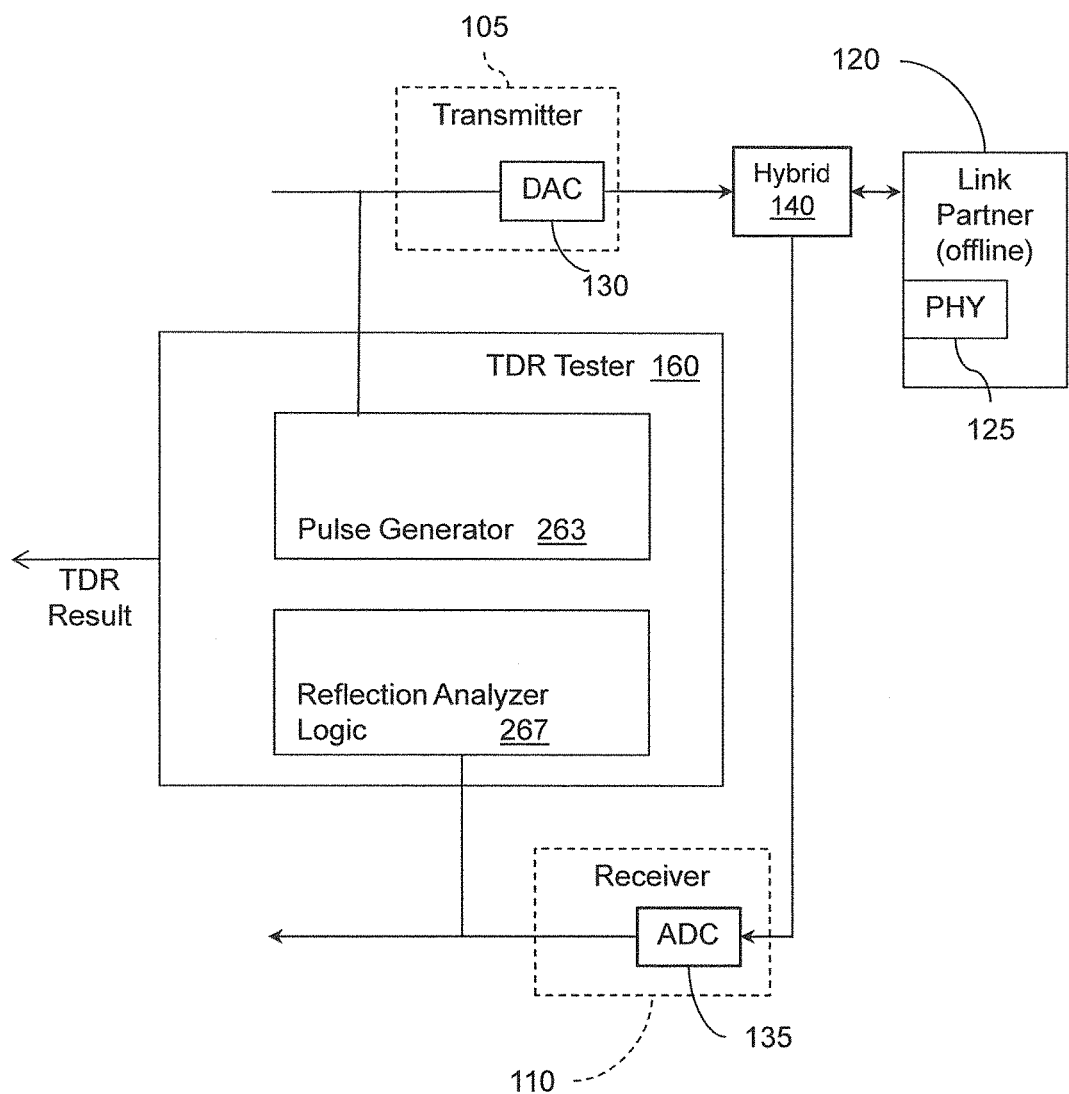
FIG. 2 illustrates one embodiment of a Time Domain Reflectometry tester that is an optional component in the power-based virtual cable test.

Referring now to FIG. 2, the TDR tester 160 employs Time Domain Reflectometry (TDR), which is a measurement technique used to determine the characteristics of electrical lines by observing reflected waveforms. An example of how TDR can be employed to test the length of a cable can be found in U.S. Pat. No. 7,808,247, which is assigned to assignee of the present invention and incorporated herein in its entirety by reference. The amplitude of the reflected signal can be determined from the impedance of a discontinuity. The TDR tester 160 includes a pulse generator 263 configured to transmit a test pulse, or "forward wave," on the cable. The TDR tester 160 includes reflection analyzer logic 267 configured to measure an elapsed time that corresponds to a time that the test pulse is transmitted in the cable until a reflected "return wave" is received. Using the elapsed time, the return wave amplitude, and a cable propagation constant, the reflection analyzer logic 267 estimates a length of the cable and can also identify a fault within the cable.

A perfectly terminated line has no attenuation and has an impedance that is matched to a source impedance. The load is equal to the line impedance. The return wave is zero for a perfectly terminated line because the load receives all of the forward wave energy. When the return wave has a very low amplitude, the reflection analyzer logic 267 may determine that the cable has no faults and report, as a TDR result, a length that is determined based on the time delay in receiving the return wave.

For open circuits, the return wave has a positive amplitude that is approximately equal to the forward wave. Thus, when the return wave is strong (e.g., has amplitude equal to 50%-100% of the amplitude of the forward wave), the reflection analyzer logic 267 will report, as the TDR result, the length of the cable and that the cable has an open circuit. For short circuits, the return wave has a strong negative amplitude (e.g., a negative amplitude that is equal in magnitude to 50%-100% of the forward wave). Thus, when the return wave has a strong negative amplitude, the reflection analyzer logic 267 will report, as the TDR result, length of the cable and that the cable has a short circuit.

As will be described in more detail with respect to FIG. 5, in one embodiment, when the link partner 120 is offline, the cable test control logic 160 will activate the TDR tester 160 when a cable test is desired. This is because sending a test pulse will not affect network traffic as the link partner is offline, and also because the link partner 120 should be online when utilizing the power-based tester 180.

Figure 3A:
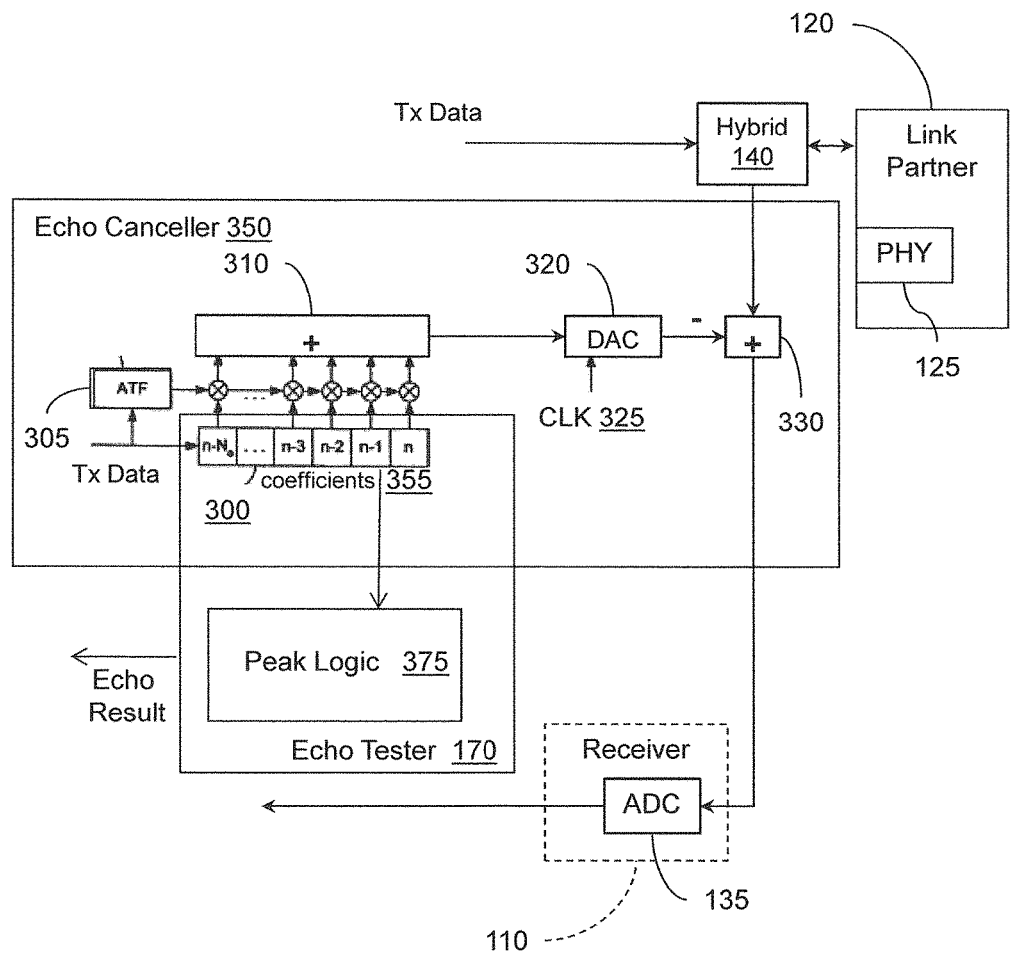
FIGS. 3A and 3B illustrate one embodiment of an echo canceller coefficient based cable tester.

FIG. 3A illustrates one embodiment of an echo tester 170. To compensate for echo signals, the apparatus 100 includes an echo canceller 350 connected to the transmitter 105 and the receiver 110. In one embodiment, the echo canceller 350 includes echo canceller coefficients 355 that are used to cancel or at least reduce echo signals. This will be described in more detail below. In one embodiment, the plurality of echo canceller coefficients 355 are maintained in a finite impulse response (FIR) filter with a plurality of taps. In some embodiments, the echo canceller coefficients 355 may be implemented in one or more shift registers, a look-up table, or other storage/memory device.

The echo tester 170 is connected to the echo canceller 350. The echo tester 170 includes peak logic 375 that is configured to determine/detect a cable fault in the cable 115 using the echo canceller coefficients 355 from the echo canceller 350. By using the echo canceller coefficients 355, a separate test pulse does not need to be transmitted over the cable 115 and thus the echo tester 170 can check the status of the cable 115 without breaking or interrupting the communication link. As will be further described below, determining a length of the cable 115 and/or determining whether a fault exists in the cable 115 based on the echo canceller coefficients 355 may provide a more accurate or more sensitive detection mechanism for determining status of a cable as compared to implementing a TDR test or a power-based cable test.

With reference to echo cancellation, a general description is as follows. As data is transmitted from the transmitter 105 through the cable 115, discontinuities in the cable 115 may cause an echo signal to be reflected back to the apparatus 100. The echo signals are then received by the receiver 110 along with actual data signals and may distort the data signals.

Echo cancellation involves recognizing the originally transmitted signal that re-appears, with some delay, in the transmitted or received signal. Once the echo signal is recognized, it can be removed by "subtracting" it from the transmitted or received signal. This technique is generally implemented using a digital signal processor (DSP), but in some embodiments can also be implemented in software, or both. Echo cancellation may be performed using echo suppressors, echo cancellers, or in some cases both. Initial echo canceller coefficients 355 may be generated from observed tests that include transmitting known test patterns through a communication link and comparing received signals to the transmitted patterns. Certain differences between the transmitted signals and the received signals can be attributed to echo signals and corresponding cancellation coefficients are generated for cancelling out the echo signals. In some embodiments, an adaptive filter (FIR) may be used to modify the coefficients during operation of the echo canceller 350 based at least in part on observed signal comparisons.

The echo tester 170 is not limited to any particular type or implementation of the echo canceller 350. The echo tester 170 is not limited to the example echo canceller 350 discussed herein but can be implemented with any other configurations that include echo canceller coefficients.

The echo canceller 350 includes a shift register 300, an adaptive cancellation filter ATF 305, and a combiner 310. Shift register 300 receives transmission data symbols TxData. The shift register 300 can have a size ($N_e$) equal to a length of the echo canceller 350. Adaptive cancellation filter 305 produces echo canceller coefficients that model impulse responses of the echo signal encountered by the receiver 110. A digital replica of the echo signal encountered by the receiver 110 is generated by multiplying the echo canceller coefficients with data symbols TxData and summing the results through the combiner 310.

The adaptive cancellation filter 305 may be implemented as an adaptive transversal filter (ATF) using, for example, the least mean squares (LMS) algorithm. The digital replica of the echo signal can be sent to combiner 310 and to a digital-to-analog converter DAC 320. The DAC 320 can be clocked with clock signal 325 to ensure that echo signals are properly cancelled out at subtractor 330 (applied to the received analog signals from the hybrid circuit 140). Timing delays that may be associated with the generation of the digital replica of the echo signal may be compensated for by appropriate time domain manipulations of the digital replica interference signal.

As previously discussed, impedance mismatches along a cable typically cause signal reflections on the cable. To cancel these reflections, echo canceller coefficients corresponding to different locations along the cable are determined and adapted. The coefficient associated with a particular location along the cable is determined by the severity of the impedance mismatch at that location. For example, the severity of the impedance mismatch is determined based on the amplitude of the echo signal received from an impedance mismatch at a particular location on the cable. The coefficients are then stored in the shift register 300 wherein one coefficient is stored in one tap. The shift register 300 may have a desired number of taps (e.g. 96 or more) wherein each successive tap/coefficient is associated with the next location along the cable wherein an impedance mismatch was found.

When the echo tester 170 is activated by the cable tester control logic 190, the peak logic 375 accesses the echo canceller coefficients in the shift register 300. The echo canceller coefficients are analyzed by the peak logic 375 to determine a cable status of the cable operatively connected to the digital signal processor. The echo result is a signal that is generated by the echo tester 170 that represents the length of the cable and/or the status of the cable (e.g. OK (no fault), short, open) based at least in part on the analysis.

In one embodiment, the peak logic 375 identifies a plurality of peaks from the reflected echo signals along the cable. For example, the plurality of peaks may include a near end peak that is a peak near a connection between the digital signal processor and the cable, and a tail end peak that is a peak some distance from the near end peak. An amplitude of the tail end peak may be determined and compared to a threshold(s). The status of the cable is then determined based at least in part on the results of the comparison between the amplitudes and the respective thresholds. The threshold(s) can be generated from observed cable characteristics and expected peak amplitudes associated with certain distances. For example observed results can be obtained from non defective cables that represent an expected tail end peak (second peak) at certain cable distances. If, from the echo canceller coefficients, the second peak is found with a value that meets or exceeds a threshold associated with a distance from the near end, this condition may represent a fault within the cable. Several techniques for detecting peaks will be described in more detail below.

Figure 3B:
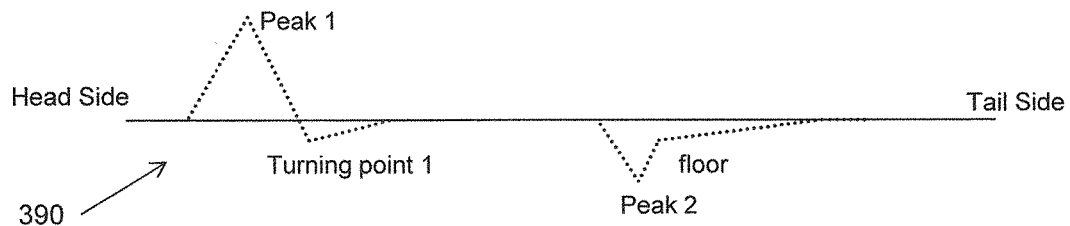

With reference to FIG. 3B, techniques and algorithms used by the peak logic 375 for finding peaks from the echo canceller coefficients are described. FIG. 3B illustrates an example diagram 390 that shows an example shape (represented by the dotted line) of coefficients. As shown in FIG. 3B, well adapted echo canceller coefficients should have two (2) peaks, named peak1 and peak2 that may occur over the cable 115. Coefficients associated on the left side of peak1 correspond to cable impedance near the link device 100, which is the device performing the cable test. Finding the exact locations and peak values of the two peaks provide for more accurate detection of the impedance and location of cable faults along the cable 115. As peak2 is more attenuated by the cable 115, it is more difficult to be correctly detected.

Algorithms for Finding Peak1

In one embodiment, the peak logic 375 analyzes echo canceller coefficients to identify peak1 from the head side to the tail side of the cable 115. The echo canceller 350 (shown in FIG. 3) stores the echo canceller coefficients 355 according to distance from the head side. For example, if there are 100 taps (0-99) that store coefficients, tap 0 is the echo canceller coefficient nearest to the head side along the cable and tap 99 is associated with the furthest distance from the head side. An echo canceller coefficient that may qualify as peak' should meet the following conditions: (1) is located between a certain range of coefficient locations (e.g. closer to the head side); (2) it is a peak (e.g. neighbor coefficients either have different signs or amplitudes are smaller); and (3) (a) its amplitude should also be larger than a certain predetermined threshold (e.g. to eliminate small peaks), or (b) its relative amplitude to the previous coefficient is larger than a threshold. The amplitude is evaluated using the absolute value of the coefficient. Finding peak values may include comparing neighboring echo canceller coefficients to identify high points, low points, and transition points (e.g. turning points: going from increasing values to decreasing values or vice versa).

Algorithms for Finding Peak2

In one embodiment, the peak logic 375 analyzes the echo canceller coefficients used to identify Peak2. Peak2 is searched from the tail side to the head side. The echo canceller coefficients are analyzed to find peak values of reflections and their distance, which will determine whether a cable fault exists or not. Peak2 is divided into two possible types: type I is a flat peak (e.g. a smooth, more rounded transition at peak like a hill shape) and type II is sharp peak (e.g. point-like shape at peak). Peak2 is considered to be found if either type is detected.

In one embodiment, finding a type I peak (flat) includes finding the echo canceller coefficient that matches the following conditions: (1) it is a peak; (2) its height should be larger than a certain predefined threshold; (3) its height should be bigger than another threshold determined by the biggest differences between neighbor coefficients on its right side (toward the tail side); and (4) the echo canceller coefficient should be a certain distance away from the head side. As stated previously, typical cable responses and characteristics may be predetermined from testing known cables. Based on these observations, peak2 can be expected to have a certain amplitude and be between certain distances along the cable (measured by thresholds). Finding peak2 outside the thresholds generates a cable fault signal.

In one embodiment, finding a type II peak (sharp) includes finding the echo canceller coefficient that matches the following conditions: (1) it is a peak; (2) its width is less than a threshold; and (3) its height should also be larger than certain predetermined threshold (determined from observed tests).

The peak width may be counted as follows. From the tail side to the head side, all points wherein the coefficients increase/decrease direction change are defined as turning points. The tail is considered as a turning point. A turning point is used as a floor for the turning points on their left side to calculate the peak amplitude. The distance between the turning point and its floor is considered as the width of this peak. The signed amplitude difference between the turning point and its floor is taken as the height of the peak. After each turning point, a counter is used to count the distance from the tail side to the head side.

As shown in FIG. 3B, coefficients may increase or decrease to the same direction slowly (drifting) before a real peak starts. The following algorithm may be used for removing the drifting. After a turning point, if the following conditions are met, the floor is not the turning point. It moves to the head side until the following conditions are both broken: (1) neighbor coefficient difference is less than a threshold; and (2) sum of difference is also less than a threshold.

Judging the Condition of a Cable

Once the peaks are found, the condition of a cable can be determined. For example, a location of a fault within a cable can be calculated by multiplying a constant by the distance between peak' and peak2. The amplitude of peak2 is compared to predetermined thresholds to determine the cable status including open, OK, or short. The thresholds may vary according to the distance between peak 1 and peak 2 from the head side to the tail side. The thresholds represent amplitude thresholds associated with a fault condition at various distances from the head side to the tail side along the cable. The thresholds corresponding to an open within a cable (referred to herein as "open thresholds") may be represented as positive values and the thresholds corresponding to a short within the cable (referred to herein as "short thresholds") may be represented as negative values. In one embodiment, if an echo canceller coefficient is found to meet or exceed either an open threshold or an short threshold, a fault condition signal is generated.

A status of "open" is determined if peak2 amplitude (at its associated distance from the head side) is larger than the positive threshold at that distance. A status of "short" is determined if peak2 amplitude is less than the negative threshold at the corresponding distance. A status of "OK" (no fault, normal condition) is determined if the peak2 amplitude is between the positive and negative thresholds.

In one embodiment, the echo tester 170 performs post processing on the peaks identified on the four pairs of twisted cables in the cable 115. For example, voting may be used to select which peak2's distance should be used to determine the length of the cable 115. An outlier peak2 (e.g., "very" different from the other three pairs' peak2s) may be discarded. The distances of the peak2s for each of the four pairs may be averaged, and so on.

As already discussed, the echo canceller coefficient-based cable testing performed by the echo tester 170 may be susceptible to errors in erroneously detecting a peak associated with a fault as the tail end peak. This is because mismatches in impedance that result in peaks can come from not only the terminator but also connectors between two cable segments. The number of taps are usually limited to save hardware resources, so the taps may be located to cancel noise from connectors or faults that are "worse" than the peak caused by the terminator. This results in reporting a shorter cable length.

The amplitude of the tail end peak is determined by the terminator's impedance mismatch and decreases as cable length increases. Even for cables without intermediate connectors, the tail end peak's amplitude may be too small to be found by peak-finding algorithms given well matched terminators. In these cases, distance results of four pairs may be different, necessitating post processing to determine an estimated cable length based on all four results. Also, the length of the cable may not be known a priori, or may have changed since assumptions about ranges of distances in which the tail end peak were made, making it difficult to know wherein to expect the second peak. The cable tester 160 addresses these problems with echo canceller coefficient-based cable testing by performing power-based testing, when possible (e.g., when the link partner 125 is online), to define an end detection range (EDR in FIG. 1) in which the echo canceller coefficient-based cable testing should detect the tail end peak. This helps prevent the erroneous cable terminator detection caused by noisy network traffic or cable faults.

Figure 4:
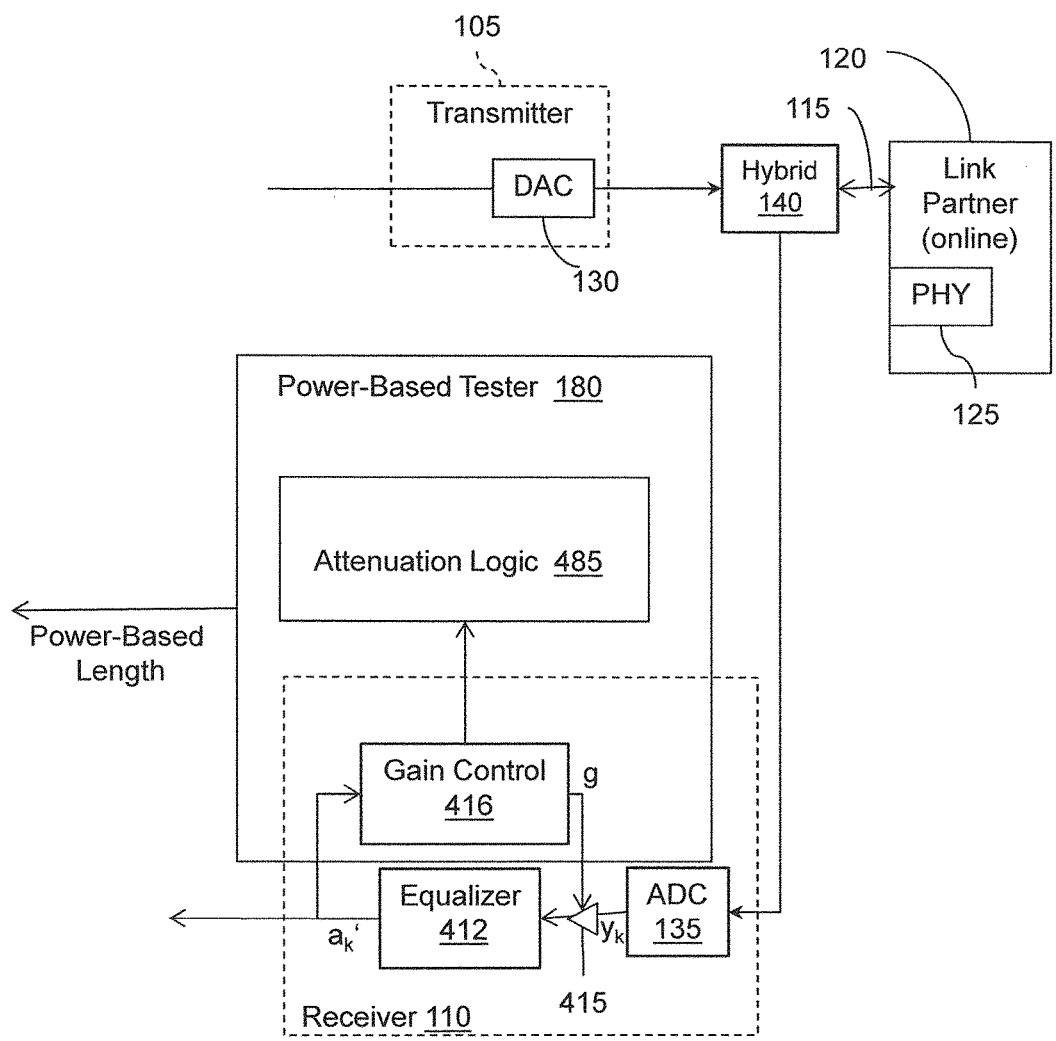
FIG. 4 illustrates one embodiment of a power-based cable tester.

Power-based cable testing leverages that fact that signal attenuation is a function of the length of a cable. Thus, if the attenuation of the signal from the link partner 120 to the receiver 110 can be measured directly, or indirectly, the cable length can be determined based on the attenuation. FIG. 4 illustrates one embodiment of a power-based tester 180 that determines a power-based cable length (PB length in FIG. 1) based on the gain of an equalizer 412 in the receiver 110. The gain of the equalizer is proportional to the attenuation of the signal from the link partner 120.

The analog to digital converter (ADC) 135 samples and holds the signal from the link partner 120 for a duration of the symbol period, which in one embodiment is 8 ns. The digitized signals $y_k$ are then input to an amplifier 415, which compensates for loss of signal that is experienced in transmission channel 115. The gain g of amplifier 415 is adjusted by gain control 416 in order to optimize the receiver function. Although amplifier 415 in FIG. 4 is shown as a digital amplifier located between the ADC 135 and the equalizer 412, the amplifier 415 can also be an analog amplifier located anywhere in before ADC 135 in the signal processing sequence of the receiver 110. Additionally, the gain shown in Table I below is unaffected by the placement of amplifier 415 in receiver 100.

The output signal from amplifier 415, $y_k$, is input to an equalizer 412. In equalizer 412, the effects of the channel distortion are countered and the equalizer 412 outputs signal $a_k'$. The gain control 416 adjusts the gain of the amplifier 415 by comparing the modulus of signal $a_k'$ with a target threshold value. The gain of the amplifier 415 compensates for the channel at loss factor 1/g.

The attenuation logic 485 computes the cable length based on the gain g. In one embodiment, the attenuation logic 485 computes the cable length using the following relationship, which is based on a previously determined mapping of gain to cable length.

$$L = [1.0232 + 7.8e^{-3}g + 2e^{-4}g^2] \qquad \text{EQ 1}$$

In another embodiment of the invention, the attenuation logic 485 compares the gain g is to a stored look-up table (not shown) to estimate the cable length. Some embodiments can extrapolate between entries in the look-up table in order to arrive at a more accurate estimate of the cable length from the gain g. Table 1 below illustrates one relationship between equalizer gain and cable length computed for a particular equalizer.

TABLE I

| Cable Length (meters) (normalized) | Amplifier Gain-g |
| --- | --- |
| 0 | 1.0 |
| 20 | 1.3 |
| 40 | 1.74 |
| 60 | 2.3 |
| 80 | 3.1 |
| 100 | 4.15 |

In various embodiments, the power-based tester 180 can use any power-based method of determining cable length. Note that because the power-based method is based on the attenuation of a signal sent from the link partner 120, the link partner 120 must be online to perform power-based testing. While having the advantage of being performed while the link partner is connected and online, power-based cable testing is not considered to be very accurate. Power-based cable testing is typically assumed to be reliable to plus or minus 15 meters, depending on the actual cable length. Thus, using power-based cable testing alone will not usually result in a sufficiently accurate measurement of the cable's length. In recognition of this deficiency of power-based cable testing, the cable test control logic 190 uses the power-based cable length to improve the accuracy of the echo tester 170.

The cable test control logic 190 selectively activates the power-based tester 180 when the link partner 120 is online to estimate a power-based cable length. Based on this estimated power-based cable length, the cable test control logic 190 defines an end detection range in which the echo canceller coefficient-based cable testing (e.g., as performed by echo tester 170) should detect the tail end peak.

Figure 5:
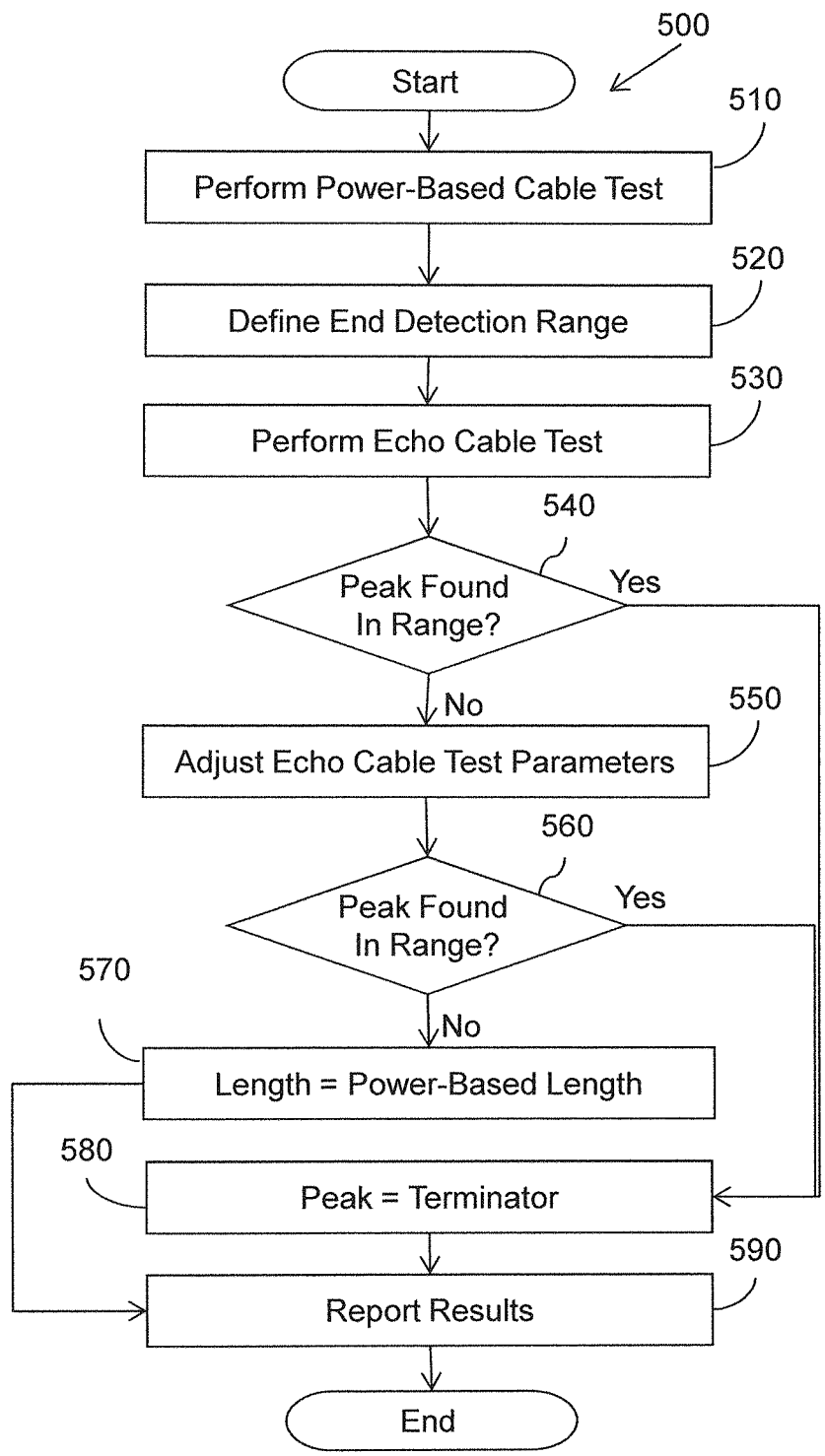
FIG. 5 illustrates one embodiment of a method for performing power-based virtual cable testing.

FIG. 5 illustrates one embodiment of a method 500 that may be performed by the cable test control logic 190 (FIG. 1) to improve the accuracy of echo canceller coefficient based cable testing (e.g., as performed by echo tester 170) using a power-based cable length estimate (e.g., as determined by power-based tester 180). In the method, the cable test control logic 190 selectively activates the various different testers in the cable tester to perform their respective cable tests. The cable test logic 190 reports a cable length that is based on the results of the cable tests.

Figure 7:
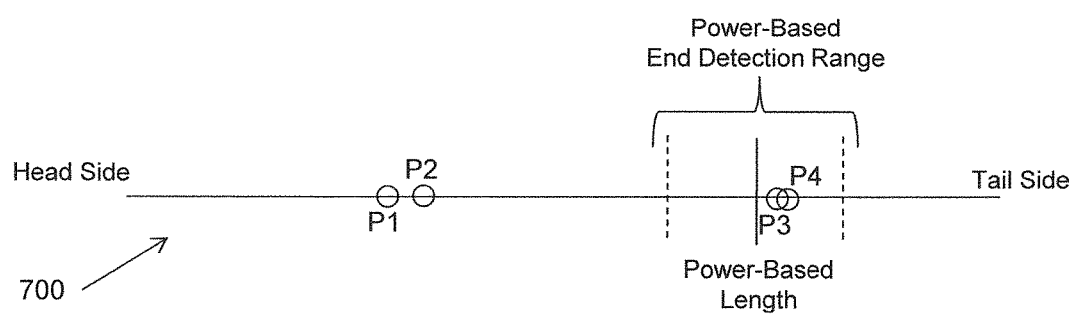
FIG. 7 illustrates an example of power-based virtual cable testing.

At 510, power-based cable testing is performed to determine a power-based cable length. At 520, an end detection range is determined based, at least in part on the power-based cable length. Referring now to FIG. 7, a representation of a cable 700 is shown with a head side and a tail side. The power-based length is designated by the distance from the head side to the solid hash line. As shown by the dashed hash lines, the end detection region is determined by adding and subtracting an expected margin of error with respect to the power-based length. The end detection region is a region of the cable in which the cable's terminator is expected to be found. In one embodiment, the margin of error is +/−15 meters, resulting in an end detection region that is 30 meters in length, centered on the power-based cable length.

Returning to FIG. 5, an echo cable test is performed at 530. Recall from FIG. 3 that the echo cable test involves using echo canceller coefficients to identify peaks in a reflected signal and deducing the distance to the cable terminator and/or the location of cable faults and connectors based on the peaks. At 540, it is determined whether a peak is found within the end detection range. If a peak is found within the end detection range, at 580, the peak is designated as corresponding to the terminator and at 590 results reporting the distance to the terminator as the cable length are provided.

In one embodiment, if a peak is not found within the end detection range, at 550 one or more peak detection parameters of the echo cable test are adjusted to increase sensitivity. In one embodiment, the detection parameters include one or more the thresholds used in peak detection as described above with reference to FIG. 3. At 560, a determination is made as to whether a peak has been found within the end detection range using the adapted detection parameters. If a peak is found within the end detection range, at 580, the peak is designated as corresponding to the terminator and at 590 results reporting the distance to the terminator as the cable length are provided.

If a peak is still not found within the end detection range, at 570 the cable length is determined to be the power-based length and the power-based length is reported at 590. In this manner, if the echo cable test is unable to identify a peak, the power-based length is reported to provide a rough estimate of the length.

Figure 6:
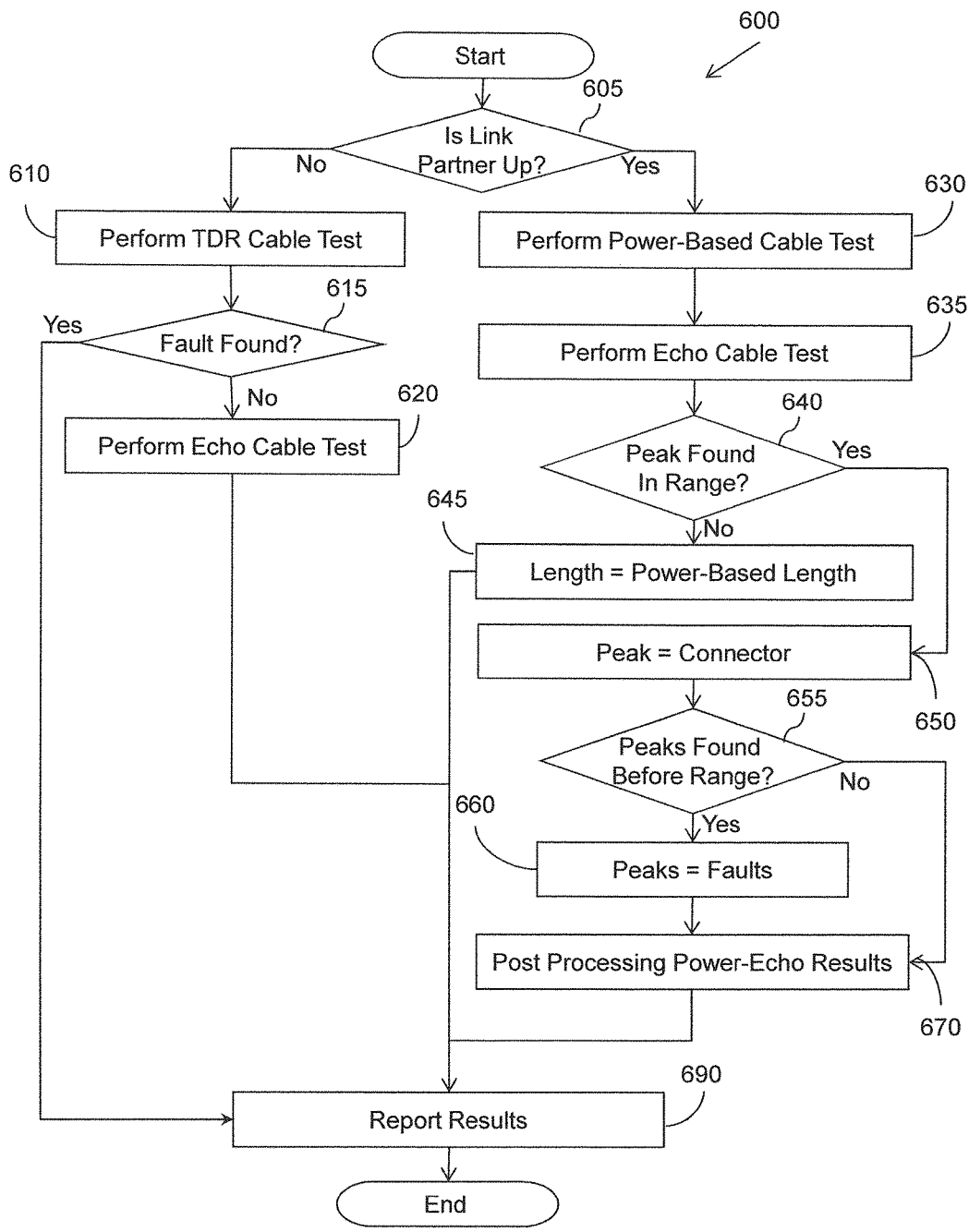
FIG. 6 illustrates another embodiment of a method for performing power-based virtual cable testing.

FIG. 6 illustrates one embodiment of a method 600 that may be performed by the cable test control logic 190 of FIG. 1. At 605, a determination is made as to whether the link partner is up or online. If the link partner is not up, at 610 a TDR cable test is performed. The TDR cable test is possible because the link partner is not online. At 615 a determination is made as to whether a fault was found by the TDR cable test. If so, the results of the TDR cable test are reported at 690. This is appropriate because the TDR cable test will detect only the most severe faults and thus if a fault is detected by the TDR cable test there is no significant advantage to performing additional cable tests. If no fault is found by the TDR cable test, at 620, an echo cable test is performed. The echo cable test may detect a length and/or faults that cannot be detected by the TDR cable test. At 690, the result of the echo cable test is reported.

If the link partner is up or online, power-based cable testing is possible. At 630 power-based cable testing is performed to determine a power-based cable length and an end detection range is determined based, at least in part, on the power-based cable length. At 635, an echo cable test is performed. Recall from FIG. 3 that the echo cable test involves using echo canceller coefficients to identify peaks in a reflected signal and deducing the distance to the cable terminator and/or the location of cable faults and connectors based on the peaks. At 640, it is determined whether a peak is found within the end detection range. If a peak is not found within the end detection range, at 645 the cable length is determined to be the power-based length and the power-based length is reported at 690. In one embodiment, prior to reporting the power-based length, the detection parameters of the echo cable test may be adjusted and subsequent attempts to detect a peak within the range may be made. If the echo cable test is unable to identify a peak within the end detection range, the power-based length is reported at 645 to provide a rough estimate of the length.

If a peak is found within the end detection range, at 650, the peak is designated as corresponding to the terminator. At 655, a determination is made as to whether any peaks were found before the end detection range, if so, these peaks are designated as faults or connectors at 660. At 670, post processing is performed on the peaks that were identified by the echo cable test. At 690 the results of the post processing from 670 are provided.

Referring to FIG. 7, one embodiment of post processing on peaks is shown. Four peaks P1-P4 have been identified. The four peaks may each be the tail end peak detected for a different pair of twisted wires in the cable under test. To determine the length of the cable, only those peaks P3 and P4 are considered to correspond to a cable terminator, thus voting or averaging techniques are used to deduce the cable length from P3 and P4. In one embodiment, the farthest peak within the end detection range is used to determine the cable length. Peaks P1 and P2 may be designated as faults or connectors.

Figure 8:
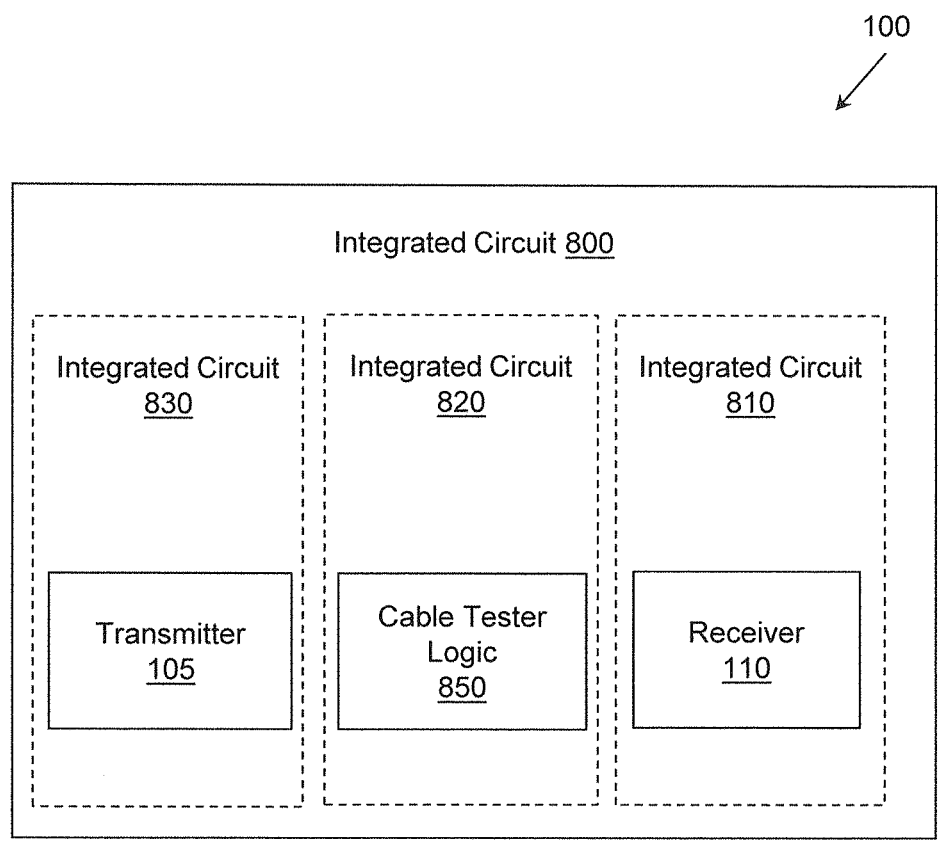
FIG. 8 illustrates one embodiment of an integrated circuit configured to perform power-based virtual cable testing.

FIG. 8 illustrates one embodiment of an integrated circuit 800 that performs power-based cable virtual cable test. In one embodiment, the integrated circuit 800 embodies the apparatus 100 described above with respect to FIGS. 1-4. The integrated circuit 800 includes an integrated circuit 810 that includes the receiver 110 (see FIG. 1) as well as an integrated circuit 830 that includes the transmitter 105. The integrated circuit 800 also includes an integrated circuit 820 that includes a cable tester logic 850. The cable tester logic 850 may embody the cable test logic 150 described above with respect to FIGS. 1-4 and may perform the methods 500 and/or 600 described above with reference to FIGS. 5 and 6, respectively. In one embodiment, the cable tester logic includes an echo tester, a power-based cable tester, and a cable test control logic. The echo tester configured to identify peaks corresponding to echo canceller coefficients that model an impulse response of reflected signals received by the receiver. The power-based cable tester is configured to determine a power-based cable length based on signal attenuation of a signal received from the link partner. The cable test control logic is configured to selectively activate one or both of the echo tester and the power-based tester and to determine a cable length based, at least in part, on the power-based cable length and the identified peaks.

With the described apparatus, methods, and equivalent embodiments, cable condition may be optimally detected a number of different network conditions. When a link partner is up, an echo canceller coefficient-based cable evaluation technique can be targeted using a power-based estimate of the cable's length. Parameters and post processing of the echo canceller coefficient-based cable evaluation technique can be adapted based on the power-based estimate of the cable's length. When a link partner is not up, a TDR cable test may be performed and followed up by an echo canceller coefficient based test when no faults are detected by the TDR test.

The following includes definitions of selected terms employed herein. The definitions include various examples and/or forms of components that fall within the scope of a term and that may be used for implementation. The examples are not intended to be limiting. Both singular and plural forms of terms may be within the definitions.

References to "one embodiment", "an embodiment", "one example", "an example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer storage medium" as used herein is a non-transitory medium that stores instructions and/or data. A computer storage medium may take forms, including, but not limited to, non-volatile media, and volatile media. Non-volatile media may include, for example, optical disks, magnetic disks, and so on. Volatile media may include, for example, semiconductor memories, dynamic memory, and so on. Common forms of a computer storage media may include, but are not limited to, a floppy disk, a flexible disk, a hard disk, a magnetic tape, other magnetic medium, an ASIC, a CD, other optical medium, a RAM, a ROM, a memory chip or card, a memory stick, and other electronic media that can store computer instructions and/or data. Computer storage media described herein are limited to statutory subject matter under 35 U.S.C. §101.

"Logic" as used herein includes a computer or electrical hardware component(s), firmware, a non-transitory computer storage medium that stores instructions, and/or combinations of these components configured to perform a function(s) or an action(s), and/or to cause a function or action from another logic, method, and/or system. Logic may include a microprocessor controlled by an algorithm, a discrete logic (e.g., ASIC), an analog circuit, a digital circuit, a programmed logic device, a memory device containing instructions that when executed perform an algorithm, and so on. Logic may include one or more gates, combinations of gates, or other circuit components. Wherein multiple logics are described, it may be possible to incorporate the multiple logics into one physical logic component. Similarly, wherein a single logic unit is described, it may be possible to distribute that single logic unit between multiple physical logic components. Logic as described herein is limited to statutory subject matter under 35 U.S.C. §101.

While for purposes of simplicity of explanation, illustrated methodologies are shown and described as a series of blocks. The methodologies are not limited by the order of the blocks as some blocks can occur in different orders and/or concurrently with other blocks from that shown and described. Moreover, less than all the illustrated blocks may be used to implement an example methodology. Blocks may be combined or separated into multiple components. Furthermore, additional and/or alternative methodologies can employ additional actions that are not illustrated in blocks. The methods described herein are limited to statutory subject matter under 35 U.S.C. §101.

To the extent that the term "includes" or "including" is employed in the detailed description or the claims, it is intended to be inclusive in a manner similar to the term "comprising" as that term is interpreted when employed as a transitional word in a claim.

While the disclosed embodiments have been illustrated and described in considerable detail, it is not the intention to restrict or in any way limit the scope of the appended claims to such detail. It is, of course, not possible to describe every conceivable combination of components or methodologies for purposes of describing the various aspects of the subject matter. Therefore, the disclosure is not limited to the specific details or the illustrative examples shown and described. Thus, this disclosure is intended to embrace alterations, modifications, and variations that fall within the scope of the appended claims, which satisfy the statutory subject matter requirements of 35 U.S.C. §101.

What is claimed is:

1. An electronic device, comprising:
    a transmitter configured to transmit signals to a link partner by way of a cable;
    a receiver configured to receive signals from the link partner by way of the cable; and
    a cable tester connected to the transmitter and the receiver, wherein the cable tester comprises:
        an echo cable tester configured to, in response to a first signal being transmitted along the cable by the transmitter, identify peaks in a second signal received by the receiver by way of the cable, wherein the second signal corresponds to a reflection of the first signal within the cable, and wherein the peaks are identified based on echo canceller coefficients;
        a power-based cable tester configured to determine a length of the cable based on an attenuation of a signal received from the link partner by way of the cable; and
        a cable test control logic configured to:
            define an end detection range based, at least in part, on the length of the cable as determined by the power-based cable tester,
            determine that a peak falls within the end detection range, and
            in response to determining that the peak falls within the end detection range, (i) designate the peak as corresponding to a terminator of the cable, and (ii) determine a length of the cable based, at least in part, on the designated peak.

2. The electronic device of claim 1, wherein the cable test control logic is further configured to:
    determine that the peak does not fall within the end detection range; and
    in response to determining that the peak does not fall within the end detection range:
        adapt one or more detection parameters associated with the echo tester; and
        control the echo tester to identify peaks using the adapted detection parameters.

3. The electronic device of claim 1, wherein the cable test control logic is further configured to:
    determine that the peak does not fall within the end detection range; and
    in response to determining that the peak does not fall within the end detection range, report the length of the cable determined from the power-based cable tester.

4. The electronic device of claim 1, wherein the cable test control logic is further configured to:
    determine that one or more peaks fall outside the end detection range; and
    designate the peaks that fall outside the detection range as corresponding to faults or cable connectors.

5. The electronic device of claim 1, wherein the cable test control logic is further configured to control post processing of peaks identified for different pairs of twisted wires in the cable based, at least in part, on the end detection range.

6. The electronic device of claim 1, further comprising:
    a time domain reflectometry (TDR) tester configured to perform a cable test in response to the TDR tester being activated, wherein a cable test comprises transmitting a test pulse though the cable and determining a TDR result based, at least in part, on reflected signals received in response to the test pulse being transmitted; and
    wherein the cable test control logic is further configured to determine whether the link partner is online or offline, and when the link partner is offline:
        selectively activate the TDR tester to perform a first cable test;
        in response to a cable fault being found by the first cable test, report the cable fault; and
        in response to a cable fault not being found by the first cable test i) selectively activate the echo tester to perform a second cable test and ii) report the result of the second cable test.

7. The electronic device of claim 1, wherein the cable test control logic is further configured to:
    determine whether the link partner is online or offline; and
    when the link partner is online selectively activate the power-based tester to determine the length of the cable.

8. A method for determining a length of a cable, the method comprising:
- determining, using an electronic device, a power-based cable length of a cable based on signal attenuation of a signal received on the cable from a link partner, the electronic device connected to the link partner via the cable;
- defining, using the electronic device, an end detection range based, at least in part, on the power-based cable length;
- identifying, using the electronic device, peaks in a reflected signal on the cable using echo canceller coefficients;
- determining, using the electronic device, that a peak from the identified peaks falls within the end detection range; and
- in response to determining that the peak falls within the end detection range,
  - (i) designating the peak as corresponding to a cable terminator; and
  - (ii) determining a length of the cable based, at least in part, on the designated peak.

9. The method of claim 8, further comprising:
- determining that a second peak from the identified peaks does not fall within the end detection range; and
- in response to determining that the second peak does not fall within the end detection range:
  - adapting one or more detection parameters used to detect peaks; and
  - repeating the identifying of peaks using the adapted detection parameters.

10. The method of claim 8, further comprising:
- determining that a second peak from the identified peaks does not fall within the end detection range; and
- in response to determining that the second peak does not fall within the end detection range, reporting the power-based cable length as the length of the cable.

11. The method of claim 8, further comprising:
- determining that one or more peaks fall outside the end detection range; and
- designating the peaks that fall outside the detection range as corresponding to faults or cable connectors.

12. The method of claim 8, further comprising controlling post processing of peaks identified for different pairs of twisted wires in the cable based, at least in part, on the end detection range.

13. The method of claim 8, further comprising:
- performing a first cable test by transmitting a test pulse though the cable and determining a TDR result based, at least in part, on reflected signals received in response to the test pulse being transmitted;
- when a cable fault is found by the first cable test, reporting the cable fault; and
- when a cable fault is not found by the first cable test i) performing a second cable test by identifying peaks in a reflected signal on the cable using echo canceller coefficients; and ii) report the result of the second cable test.

14. The method of claim 8, further comprising:
- determining that the link partner is online; and
- when the link partner is online selectively determining the power-based cable length.

15. An integrated circuit device, comprising:
- a transmitter configured to transmit signals to a cable;
- a receiver configured to receive signals from the cable; and
- cable tester logic, coupled to the receiver, comprising:
  - an echo tester configured to identify peaks corresponding to echo canceller coefficients that model an impulse response of reflected signals received by the receiver by way of the cable;
  - a power-based cable tester configured to determine a power-based cable length of the cable based on an attenuation of a signal received from a link partner by way of the cable; and
  - cable test control logic configured to selectively activate one or both of the echo tester and the power-based tester and to determine a cable length of the cable based, at least in part, on the power-based cable length and the identified peaks.

16. The device of claim 15, wherein the cable test control logic is further configured to:
- define an end detection range based, at least in part, on the power-based cable length;
- determine that a first peak falls within the end detection range;
- designate the first peak as corresponding to a cable terminator;
- determine that a second peak falls outside the end detection range; and
- designate the second peak as a connector or a fault.

17. The device of claim 16, wherein the cable test control logic is further configured to:
- adapt one or more detection parameters associated with the echo tester; and
- control the echo tester to identify the peaks using the adapted detection parameters.

18. The device of claim 15, further comprising:
- a time domain reflectometry (TDR) tester configured to perform a cable test in response to the TDR tester being activated, wherein a cable test comprises transmitting a test pulse though the cable and determining a TDR result based, at least in part, on reflected signals received in response to the test pulse being transmitted; and
- wherein the cable test control logic is further configured to determine whether the link partner is online or offline, and when the link partner is offline:
  - selectively activate the TDR tester to perform a first cable test;
  - when a cable fault is found by the first cable test, report the cable fault; and
  - when a cable fault is not found by the first cable test i) activate the echo tester to perform a second cable test and ii) report the result of the second cable test.

19. The device of claim 15, wherein the cable test control logic is further configured to:
- determine whether the link partner is online or offline; and
- when the link partner is online activate the power-based tester to determine the power-based cable length.

* * * * *